United States Patent [19]

Berg et al.

[11] Patent Number: 4,935,100

[45] Date of Patent: Jun. 19, 1990

[54] DEHYDRATION OF FORMIC ACID BY EXTRACTIVE DISTILLATION

[75] Inventors: Lloyd Berg, 1314 S. 3rd Ave., Bozeman, Mont. 59715; Kraig M. Wendt; Rudolph J. Szabados, both of Bozeman, Mont.

[73] Assignee: Lloyd Berg, Bozeman, Mont.

[21] Appl. No.: 357,892

[22] Filed: May 30, 1989

[51] Int. Cl.$^5$ .................. B01D 3/40; C07C 51/44; C07C 53/02

[52] U.S. Cl. .................. 203/15; 203/51; 203/56; 203/60; 203/61; 203/62; 203/63; 203/65; 562/609

[58] Field of Search .................. 203/15, 16, 51, 61, 203/62, 63, 56, 65, 60; 562/609

[56] References Cited

U.S. PATENT DOCUMENTS

| | | | |
|---|---|---|---|
| 2,588,268 | 3/1905 | Mercer et al. | 203/16 |
| 4,642,166 | 2/1987 | Berg et al. | 203/15 |
| 4,729,818 | 3/1988 | Berg | 203/16 |
| 4,735,690 | 4/1988 | Berg et al. | 203/15 |
| 4,786,370 | 11/1988 | Berg | 203/61 |
| 4,877,490 | 10/1989 | Berg et al. | 203/15 |

FOREIGN PATENT DOCUMENTS 445645 12/1974 U.S.S.R. .................. 203/61

*Primary Examiner*—Wilbur Bascomb

[57] ABSTRACT

Formic acid cannot be completely removed from formic acid and water mixtures by distillation because of the presence of the maximum azeotrope. Formic acid can be readily removed from formic acid - water mixtures by extractive distillation in which the extractive agent is a benzoic acid derivative mixed with certain higher boiling organic compounds. Examples of effective agents are: o-toluic acid and heptanoic acid; 2-benzoylbenzoic acid and methyl salicylate; p-hydroxybenzoic acid, pelargonic acid and 2-hydroxyacetophenone.

1 Claim, No Drawings

DEHYDRATION OF FORMIC ACID BY EXTRACTIVE DISTILLATION

FIELD OF THE INVENTION

This invention relates to a method for dehydrating formic acid using certain higher boiling liquids as the agent in extractive distillation.

DESCRIPTION OF PRIOR ART

Extractive distillation is the method of separating close boiling compounds or azeotropes by carrying out the distillation in a multi-plate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compouds in a direction to make the separation on each plate greater and thus require either fewer plates to effect the same separation or make possible a greater degree of separation with the same number of plates. When the compounds to be separated normally form an azeotrope, the proper agents will cause them to boil separately during the extractive distillation and thus make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with lowest boiling component. This usually requires that the extractive agent boil twenty Centigrade degrees or more than the lowest boiling component.

At the bottom of a continuous column, the less volatile components of the close boiling mixtures and the extractive agent are continuously removed from the column. The usual methods of separation of these two components are the use of another rectification column, cooling and phase separation or solvent extraction.

There are currently two commercial methods for manufacturing formic acid. One is the reaction of caustic soda with carbon monoxide under pressure to produce sodium formate. This is then hydrolysed with sulfuric acid to yield the formic acid. The other is to obtain the formic acid as a by-product from the oxidation of n-butane. Both of these processes yield an aqueous mixture of formic acid. However the components of this mixture cannot be separated by conventional rectification because formic acid boils at 100.8° C., only 0.8° C. above water and because these two form a maximum azeotrope boiling at 107.2° C. and containing 22.5 wt.% water. Thus it is impossible to separate completely formic acid from water by rectification because of the closeness of the boiling points and because as soon as the maximum azeotrope composition is attained, no further change in composition will occur.

Extractive distillation would be an attractive method of effecting the separation of formic acid from water if agents can be found that (1) will break the formic acid—water azeotrope and (2) are easy to recover from formic acid, that is, form no azeotrope with formic acid and boil sufficiently above formic acid to make the separation by rectification possible with only a few theoretical plates.

Extractive distillation typically requires the addition of an equal amount to twice as much extractive agent as the formic acid—water on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required if the separation is done by azeotropic distillation. Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is desirable that the extractive agent be miscible with formic acid otherwise it will form a two-phase azeotrope with the formic acid in the recovery column and some other method of separation will have to be employed. Recent attempts to separate formic acid from water were reported by Kokai, Japanese Patent 82 24,324, Feb. 8, 1982 who used amines or phosphate esters to separate formic acid from water. Kawabata,, Higuchi & Yoshida, J. Bull. Chem. Soc. Japan, 1981, 54(11), 3253-8 used poly(4-vinylpyridine) to remove the water from formic acid. Jahn, Est German Patent 133,559, Jan 10, 1979 separated acetic acid-formic acid-water mixtures in three successive columns and only got a partial dehydration of the formic acid. Berg & Yeh, U.S. Pat. No. 4,642,166 used sulfones to effect this separation by extractive distillation.

OBJECTIVE OF THE INVENTION

The object of this invention is to provide a process or method of extractive distillation that will enhance the relative volatility of water from formic acid in their separation in a rectification column. It is a further object of this invention to identify suitable extractive distillation agents which will eliminate the formic acid-water azeotrope and make possible the production of pure formic acid and water by rectification. It is a further object of this invention to identify organic compounds which are stable, can be separated from formic acid by rectification with relatively few plates and can be recycled to the extractive distillation column and reused with little decomposition.

SUMMARY OF THE INVENTION

The objects of the invention are provided by a process for separating impure formic acid from water which entails the use of certain oxygenated, nitrogenous or sulfur containing organic compounds as the agent in extractive distillation as the agent in extractive distillation.

TABLE 1

| Effective Extractive Distillation Agents | | | | |
|---|---|---|---|---|
| Compounds | Ratios | | Relative Volatility | |
| Hexanoic acid (HxAc) | 1 | 6/5 | 1.6 | 1.8 |
| HxAc, Acetophenone | $(1/2)^2$ | $(3/5)^2$ | 2.0 | 2.4 |
| HxAc, Benzoic acid | " | " | 1.6 | 1.8 |
| HxAc, Benzonitrile | " | " | 1.6 | 1.7 |
| HxAc, Benzyl benzoate | " | " | 1.7 | 1.8 |
| HxAc, Butyl benzoate | " | " | 1.6 | 2.1 |
| HxAc, Cyclohexanone | " | " | 1.8 | 2.2 |

TABLE 1-continued
Effective Extractive Distillation Agents

| Compounds | Ratios | | Relative Volatility | |
|---|---|---|---|---|
| HxAc, Decanoic acid | " | " | 1.7 | 2.0 |
| HxAc, Diisobutyl ketone | " | " | 1.3 | 1.7 |
| HxAc, Dipropylene glycol dibenzoate | " | " | 1.5 | 1.8 |
| HxAc, Diethylene glycol dibenzoate | " | " | 1.6 | 2.0 |
| HxAc, Heptanoic acid | " | " | 2.0 | 2.4 |
| HxAc, 2-Heptanone | " | " | 1.7 | 1.7 |
| HxAc, 2-Hydroxy acetophenone | " | " | 1.7 | 1.8 |
| HxAc, 4-Hydroxy acetophenone | " | " | 1.5 | 1.5 |
| HxAc, Isophorone | " | " | 1.9 | 2.5 |
| HxAc, Methyl amyl ketone | " | " | 1.8 | 2.1 |
| HxAc, Methyl benzoate | " | " | 1.8 | 1.8 |
| HxAc, Methyl phenyl acetate | " | " | 1.8 | 2.4 |
| HxAc, Nitrobenzene | " | " | 1.6 | 1.8 |
| HxAc, Phenyl acetate | " | " | 1.2 | 1.2 |
| HxAc, Methyl isoamyl ketone | " | " | 1.4 | 1.8 |
| HxAc, Acetophenone (AcPh), Decanoic acid | $(1/3)^3$ | $(2/5)^3$ | 2.1 | 2.2 |
| HxAc, AcPh, Heptanoic acid | " | " | 2.2 | 2.5 |
| HxAc, AcPh, Nitrobenzene | " | " | 1.8 | 1.9 |
| HxAc, AcPh, Octanoic-Decanoic acids (Octa-Deca) | " | " | 2.1 | 2.3 |
| HxAc, AcPh, 2-Hydroxy acetophenone | " | " | 1.9 | 1.8 |
| HxAc, AcPh, Octanoic acid | " | " | 2.2 | 2.3 |
| HxAc, AcPh, Pelargonic acid | " | " | 1.9 | 2.2 |
| HxAc, AcPh, Salicyclic acid | " | " | 1.4 | 1.5 |
| HxAc, Pelargonic acid, Butyl benzoate | " | " | 1.8 | 1.9 |
| HxAc, Cinnamic acid, Benzyl benzoate | " | " | 1.4 | 1.2 |
| HxAc, Cinnamic acid, Heptanoic acid | " | " | 2.2 | 1.7 |
| HxAc, Decanoic acid, Cyclohexanone | " | " | 1.6 | 1.7 |
| HxAc, Diethylene glycol dibenzoate, Diisobutyl ketone | " | " | 1.4 | 1.7 |
| HxAc, Methyl n-amyl ketone, Nitrobenzene | " | " | 1.8 | 2.1 |
| HxAc, Methyl benzoate, Octa-Deca acids | " | " | 1.9 | 2.1 |
| HxAc, Methyl benzoate, Pelargonic acid | " | " | 1.6 | 1.9 |
| HxAc, Methyl salicylate, Glutaric acid | " | " | 1.7 | 1.7 |
| HxAc, Methyl salicylate, Octanoic acid | " | " | 1.7 | 1.8 |
| HxAc, Methyl salicylate, m-Toluic acid | " | " | 1.8 | 2.3 |
| HxAc, Isophorone, Diethylene glycol dibenzoate | $(1/3)^3$ | $(2/5)^3$ | 2.4 | 2.5 |
| HxAc, Isophorone, Dipropylene glycol dibenzoate | " | " | 2.8 | 1.9 |
| HxAc, Isophorone, Diisobutyl ketone | " | " | 1.7 | 2.0 |
| HxAc, Isophorone, 2-Hydroxy acetophenone | " | " | 2.1 | 2.3 |
| HxAc, Isophorone, 4-Hydroxy acetophenone | " | " | 2.1 | 2.4 |
| HxAc, Isophorone, Neodecanoic acid | " | " | 2.1 | 2.6 |
| HxAc, 2-Hydroxy acetophenone, 2-Heptanone | " | " | 1.8 | 1.7 |
| HxAc, Dipropylene glycol dibenzoate, Methyl amyl acetate | " | " | 1.6 | 1.5 |
| HxAc, AcPh, Neodecanoic acid, Methyl benzoate | $(1/4)^4$ | $(1/3)^4$ | 1.7 | 2.1 |
| Heptanoic acid (HpAc) | 1 | 6/5 | 1.8 | 2.0 |
| HpAc, Adipic acid | $(1/2)^2$ | $(3/5)^2$ | 1.6 | 1.8 |
| HpAc, n-Amyl acetate | " | " | 1.3 | 1.4 |
| HpAc, Azelaic acid | " | " | 1.9 | 2.0 |
| HpAc, Benzoic acid | " | " | 1.7 | 1.4 |
| HpAc, Benzyl benzoate | " | " | 1.5 | 1.8 |
| HpAc, Cinnamic acid | " | " | 1.3 | 1.8 |
| HpAc, Cyclohexanone | " | " | 3.1 | 3.5 |
| HpAc, Decanoic acid | " | " | 1.7 | 1.7 |
| HpAc, Diisobutyl ketone | " | " | 1.8 | 1.9 |
| HpAc, Dipropylene glycol dibenzoate | " | " | 1.3 | 1.6 |
| HpAc, Dodecanedioic acid | " | " | 1.3 | 2.0 |
| HpAc, Ethyl butyl ketone | " | " | 1.6 | 1.8 |
| HpAc, 2-Hydroxy acetophenone | " | " | 1.7 | 1.9 |
| HpAc, Isophorone | " | " | 2.0 | 2.6 |
| HpAc, Methly n-amyl ketone | " | " | 2.0 | 2.1 |
| HpAc, Methyl isoamyl ketone | " | " | 1.4 | 1.6 |
| HpAc, Methyl salicylate | " | " | 1.8 | 1.6 |
| HpAc, Nitrobenzene | " | " | 1.6 | 1.8 |
| HpAc, 3-Nitrotoluene | " | " | 1.4 | 1.6 |
| HpAc, o-Toluic acid | " | " | 1.3 | 1.5 |
| HpAc, Diethylene glycol dibenzoate | " | " | 1.5 | 1.7 |
| HpAc, AcPh, Benzoic acid | $(1/3)^3$ | $(2/5)^3$ | 1.7 | 1.5 |
| HpAc, AcPh, Decanoic acid | " | " | 1.6 | 1.7 |
| HpAc, AcPh, Dipropylene glycol dibenzoate | " | " | 1.5 | 1.8 |
| HpAc, AcPh, Glutaric acid | " | " | 1.7 | 2.3 |
| HpAc, AcPh, Nitrobenzene | " | " | 1.7 | 1.8 |
| HpAc, AcPh, Octa-Deca acids | " | " | 2.4 | 1.4 |
| HpAc, AcPh, Pelargonic acid | " | " | 2.2 | 2.5 |
| HpAc, Benzyl benzoate, Benzoic acid | " | " | 1.4 | 1.6 |
| HpAc, Benzyl benzoate, Pelargonic acid | " | " | 1.7 | 2.2 |
| HpAc, Decanoic acid, Butyl benzoate | " | " | 1.5 | 1.5 |
| HpAc, Decanoic acid, Cyclohexanone | " | " | 1.7 | 1.7 |
| HpAc, Decanoic acid, 2-Heptanone | " | " | 1.7 | 1.7 |
| HpAc, Decanoic acid, Methyl benzoate | " | " | 1.7 | 2.0 |
| HpAc, 2-Hydroxy acetophenone, Adipic acid | $(1/3)^3$ | $(2.5)^3$ | 2.3 | 2.1 |
| HpAc, 2-Hydroxy acetophenone, Azelaic acid | " | " | 1.7 | 2.6 |
| HpAc, 2-Hydroxy acetophenone, Cinnamic acid | " | " | 2.0 | 2.5 |
| HpAc, 2-Hydroxy acetophenone, Dodecanedioic acid | " | " | 2.1 | 2.8 |
| HpAc, 2-Hydroxy acetophenone, o-Toluic acid | " | " | 1.8 | 1.9 |
| HpAc, 4-Hydroxy acetophenone, Dipropylene glycol dibenzoate | " | " | 1.9 | 2.2 |
| HpAc, Amyl acetate, Dipropylene glycol dibenzoate | " | " | 1.6 | 1.4 |
| HpAc, Diisobutyl ketone, Diethylene glycol dibenzoate | " | " | 1.6 | 1.6 |
| HpAc, Isophorone, Diethylene glycol dibenzoate | " | " | 2.0 | 3.0 |
| HpAc, Isophorone, Dipropylene glycol dibenzoate | " | " | 2.4 | 2.1 |
| HpAc, Isophorone, Dissobutyl ketone | " | " | 1.6 | 1.8 |
| HpAc, Isophorone, Methyl salicylate | " | " | 1.6 | 1.8 |
| HpAc, Isophorone, 3-Nitrotoluene | " | " | 1.7 | 1.8 |
| HpAc, Isophorone, Octa-Deca acids | " | " | 2.3 | 2.9 |
| HpAc, Cyclohexanone, Dipropylene glycol dibenzoate | " | " | 1.7 | 1.8 |
| HpAc, Cyclohexanone, Hexanoic acid | " | " | 2.4 | 3.0 |
| HpAc, Cyclohexanone, Neodecanoic acid | " | " | 1.9 | 1.8 |
| HpAc, Methyl salicylate, Hexanoic acid | " | " | 1.5 | 1.7 |
| HpAc, Methyl salicylate, Pelargonic acid | " | " | 1.4 | 1.6 |
| HpAc, Neodecanoic acid, Diisobutyl ketone | " | " | 1.6 | 1.8 |
| HpAc, Neodecanoic acid, Ethyl butyl ketone | " | " | 1.6 | 1.8 |
| HpAc, Neodecanoic acid, Methyl isoamyl ketone | " | " | 1.7 | 1.8 |
| Octanoic acid (OcAc), | $(1/2)^2$ | $(3.5)^2$ | 1.8 | 2.0 |

TABLE 1-continued

Effective Extractive Distillation Agents

| Compounds | Ratios | | Relative Volatility | |
|---|---|---|---|---|
| Acetophenone | | | | |
| OcAc, Cyclohexanone | " | " | 1.8 | 2.2 |
| OcAc, Diethylene glycol dibenzoate | " | " | 1.3 | 1.6 |
| OcAc, 2-Heptanone | " | " | 1.4 | 1.6 |
| OcAc, Isophorone | " | " | 2.7 | 3.0 |
| OcAc, Methyl i-Amyl ketone | " | " | 1.8 | 2.0 |
| OcAc, Nitrobenzene | " | " | 1.6 | 2.0 |
| OcAc, Methyl salicylate | " | " | 1.6 | 1.7 |
| OcAc, Acetophenone, Glutaric acid | $(1.3)^3$ | $(2/5)^3$ | 1.8 | 1.9 |
| OcAc, Acetophenone, Methyl n-amyl ketone | " | " | 1.8 | 2.1 |
| OcAc, Acetophenone, nitrobenzene | " | " | 1.4 | 2.0 |
| OcAc, Decanoic acid, Cyclohexanone | " | " | 2.1 | 3.1 |
| OcAc, Isophorone, Diethylene glycol dibenzoate | " | " | 3.2 | 3.5 |
| OcAc, Isophorone, Neodecanoic acid | " | " | 1.7 | 2.1 |
| OcAc, Dipropylene glycol dibenzoate, 2-Heptanone | " | " | 1.5 | 1.8 |
| OcAc, Methyl salicylate, m-Toluic acid | " | " | 2.0 | 1.6 |
| Octanoic-Decanoic acid Mixture (Octa-Deca) | 1 | 6/5 | 1.6 | 1.4 |
| Octa-Deca, Acetophenone | $(1/2)^2$ | $(3/5)^2$ | 2.2 | 2.4 |
| Octa-Deca, Acetophenone | $(1/2)^2$ | $(3/5)^2$ | 2.2 | 2.4 |
| Octa-Deca, Benzyl benzoate | " | " | 1.4 | 1.3 |
| Octa-Deca, Cyclohexanone | " | " | 1.8 | 1.8 |
| Octa-Deca, Diethylene glycol dibenzoate | " | " | 1.4 | 1.5 |
| Octa-Deca, Dipropylene glycol dibenzoate | " | " | 1.5 | 2.2 |
| Octa-Deca, Ethyl benzoate | " | " | 1.7 | 1.6 |
| Octa-Deca, Hexanoic acid | $(1/2)^2$ | $(3/5)^2$ | 1.7 | 1.9 |
| Octa-Deca, Isphorone | " | " | 2.5 | 2.4 |
| Octa-Deca, Methyl n-amyl ketone | " | " | 1.9 | 2.2 |
| Octa-Deca, Methyl isoamyl ketone | " | " | 1.8 | 2.0 |
| Octa-Deca, Methyl benzoate | " | " | 1.8 | 1.9 |
| Octa-Deca, Methyl salicylate | " | " | 1.7 | 1.8 |
| Octa-Deca, Nitrobenzene | " | " | 1.3 | 1.4 |
| Octa-Deca, Acetophenone, Cinnamic acid | $(1/3)^3$ | $(2/5)^3$ | 2.0 | 1.7 |
| Octa-Deca, Acetophenone, Methyl n-amyl ketone | " | " | 2.2 | 2.4 |
| Octa-Deca, Acetophenone, Methyl salicylate | " | " | 1.8 | 1.8 |
| Octa-Deca, Cyclohexanone, Decanoic acid | " | " | 1.5 | 1.9 |
| Octa-Deca, Cyclohexanene, Dipropylene glycol dibenzoate | " | " | 1.6 | 1.9 |
| Octa-Deca, Isophorone, Diethylene glycol dibenzoate | " | " | 1.9 | 2.1 |
| Octa-Deca, Isophorone, Dipropylene glycol dibenzoate | " | " | 1.9 | 2.3 |
| Octa-Deca, Isophorone, Nitrobenzene | " | " | 1.6 | 1.7 |
| Pelargonic acid (PgAc), Adipic acid | $(1/2)^2$ | $(3/5)^2$ | 1.6 | 1.8 |
| PgAc, Cinnamic acid | " | " | 1.4 | 1.8 |
| PgAc, Cyclohexanone | " | " | 1.8 | 2.4 |
| PgAc, Diisoamyl ketone | " | " | 1.6 | 1.6 |
| PgAc, Diisobutyl ketone | " | " | 1.5 | 1.7 |
| PgAc, Dipropylene glycol dibenzoate | " | " | 1.5 | 2.0 |
| PgAc, Dodecanedioic acid | " | " | 1.8 | 1.2 |
| PgAc, Ethyl butyl ketone | " | " | 1.4 | 1.7 |
| PgAc, 2-Hydroxy acetophenone | " | " | 1.5 | 1.5 |
| PgAc, p-Hydroxy benzoic acid | " | " | 1.5 | 2.0 |
| PgAc, Isophorone | " | " | 2.2 | 2.4 |
| PgAc, Methyl n-amyl ketone | " | " | 1.7 | 1.9 |
| PgAc, Methyl phenyl acetate | " | " | 1.6 | 1.7 |
| PgAc, 2-Nitrotoluene | " | " | 1.6 | 1.8 |
| PgAc, 3-Nitrotoluene | " | " | 1.5 | 2.0 |
| PgAc, Salicylic acid | " | " | 1.6 | 2.1 |
| PgAc, Sebacic acid | " | " | 1.4 | 1.7 |
| PgAc, o-Toluic acid | " | " | 1.5 | 1.4 |
| PgAc, Toluic acid | " | " | 1.4 | 2.2 |
| PgAc, p-Toluic acid | " | " | 1.4 | 1.5 |
| PgAc, Acetophenone (AcPh), | $(1/3)^3$ | $(2/5)^3$ | 1.1 | 1.7 |
| PgAc, AcPh, Decanoic acid | " | " | 1.8 | 1.9 |
| PgAc, AcPh, Dipropylene glycol dibenzoate | " | " | 1.8 | 2.1 |
| PgAc, AcPh, Isophorone | " | " | 2.4 | 2.5 |
| PgAc, AcPh, Methyl n-amyl ketone | " | " | 1.8 | 2.1 |
| PgAc, AcPh, Nitrobenzene | " | " | 1.9 | 2.1 |
| PgAc, AcPh, Octanoic - Decanoic acids | " | " | 2.2 | 2.3 |
| PgAc, AcPh, Sulfolane | " | " | 2.4 | 2.7 |
| PgAc, Benzyl benzoate, Diisobutyl ketone | $(1/3)^3$ | $(2/5)^3$ | 1.1 | 1.1 |
| PgAc, Benzonitrile, Hexanoic acid | " | " | 1.6 | 1.6 |
| PgAc, Benzyl benzoate, Hexanoic acid | " | " | 2.0 | 1.9 |
| PgAc, Cyclohexanone, Decanoic acid | " | " | 2.1 | 2.4 |
| PgAc, Dipropylene glycol dibenzoate, m-Toluic acid | " | " | 1.3 | 1.6 |
| PgAc, 2-Hydroxy acetophenone (2-HAP), Adipic acid | " | " | 1.5 | 1.7 |
| PgAc, 2-HAP, Cinnamic acid | " | " | 2.2 | 2.0 |
| PgAc, 2-HAP, Dodecanedioic acid | " | " | 1.1 | 1.1 |
| PgAc, 2-HAP, p-Hydroxy benzoic acid | " | " | 2.0 | 1.7 |
| PgAc, 2-HAP, Sebacic acid | " | " | 1.6 | 2.5 |
| PgAc, 2-HAP, o-Toluic acid | " | " | 1.6 | 1.5 |
| PgAc, 2-HAP, p-Toluic acid | " | " | 1.8 | 1.9 |
| PgAc, 4-Hydroxy acetophenone, Dipropylene glycol dibenzoate | " | " | 1.5 | 1.7 |
| PgAc, Isophorone, Decanoic acid | " | " | 2.0 | 2.6 |
| PgAc, Isophorone, Diethylene glycol dibenzoate | " | " | 2.0 | 2.2 |
| PgAc, Isophorone, Dipropylene glycol dibenzoate | " | " | 2.1 | 3.1 |
| PgAc, Isophorone, Diisobutyl ketone | " | " | 2.2 | 2.1 |
| PgAc, Isophorone, Heptanoic acid | " | " | 1.7 | 2.3 |
| PgAc, Isophorone, Methyl phenyl acetate | " | " | 1.8 | 2.4 |
| PgAc, Isophorone, 2-Nitrotoluene | " | " | 2.2 | 2.4 |
| PgAc, Isophorone, 3 Nitrotoluene | " | " | 2.0 | 2.3 |
| PgAc, Isophorone, Octanoic - Decanoic acids | " | " | 2.5 | 2.5 |
| PgAc, Diisobutyl ketone, Hexanoic acid | " | " | 1.5 | 1.9 |
| PgAc, Ethyl benzoate, Octanoic - Decanoic acids | " | " | 1.3 | 1.3 |
| PgAc, Ethyl butyl ketone, Neodecanoic acid | " | " | 1.8 | 1.7 |
| PgAc, Methyl n-amyl ketone, Decanoic acid | " | " | 2.0 | 2.2 |
| PgAc, Methyl isoamyl ketone, Dipropylene glycol dibenzoate | " | " | 1.4 | 1.8 |
| PgAc, Methyl isoamyl ketone, Hexanoic acid | " | " | 1.6 | 1.9 |
| PgAc, Methyl isoamyl ketone, Octanoic - Decanoic acids | " | " | 1.8 | 2.1 |
| PgAc, Methyl benzoate, Cinnamic acid | " | " | 1.6 | 1.6 |
| PgAc, Methyl benzoate, Dipropylene glycol dibenzoate | " | " | 1.5 | 2.0 |
| PgAc, Methyl benzoate, Glutaric acid | " | " | 1.5 | 1.9 |
| PgAc, Methyl benzoate, Octanoic - Decanoic acids | " | " | 1.9 | 1.8 |
| PgAc, Methyl salicylate, Dipropylene glycol dibenzoate | " | " | 1.4 | 2.1 |
| PgAc, Methyl salicylate, Hexanoic acid | " | " | 2.0 | 2.0 |

TABLE 1-continued
Effective Extractive Distillation Agents

| Compounds | Ratios | | Relative Volatility | |
|---|---|---|---|---|
| PgAc, Salicylic acid, Itaconic acid | " | " | 1.8 | 2.0 |
| Decanoic acid (DcAc), Acetophenone | (1/2)[2] | (3/5)[2] | 1.7 | 1.8 |
| DcAc, Butyl benzoate | " | " | | |
| DcAc, Cyclohexanone | " | " | 1.9 | 2.0 |
| DcAc, Dipropylene glycol dibenzoate | " | " | 2.3 | 2.6 |
| DcAc, Isophorone | " | " | 2.2 | 2.7 |
| DcAc, Methyl n-amyl ketone | " | " | 2.8 | 2.3 |
| DcAc, Methyl isoamyl ketone | " | " | 1.4 | 1.7 |
| DcAc, Methyl benzoate | " | " | 1.9 | 2.0 |
| DcAc, Dipropylene glycol | (1/3)[3] | (2.5)[3] | 2.4 | 2.8 |
| DcAc, DPGB, 2-Heptanone | " | " | 1.5 | 1.5 |
| DcAc, DPGB, Methyl isoamyl ketone | " | " | 1.6 | 1.8 |
| DcAc, DPGB, Methyl benzoate | " | " | 1.9 | 2.0 |
| DcAc, Acetophenone, Isophorone | " | " | 2.5 | 2.7 |
| Neodecanoic acid (NdAc), | (1/2)[2] | (3/5)[2] | 1.7 | 2.3 |
| NdAc, Isophorone | " | " | 1.2 | 2.5 |
| NdAc, Methyl n-amyl ketone | " | " | 1.2 | 1.6 |
| NdAc, Acetcone, Methyl | (1/3)[3] | (2/5)[3] | 1.8 | 1.7 |
| NdAc, Methyl benzoate, Nitrobenzene | " | " | 1.6 | 1.8 |
| Benzoic acid (BzAc) Acetophenone | (1/2)[2] | (3/5)[2] | 1.8 | 1.7 |
| BzAc, Benzonitrile | " | " | 1.6 | 1.7 |
| BzAc, Butyl benzyl phthalate | " | " | 1.7 | 2.1 |
| BzAc, Dibutyl phthalate | " | " | 1.4 | 1.4 |
| BzAc, Isophorone | " | " | 1.9 | 2.0 |
| BzAc, Methyl salicylate | " | " | 1.6 | 1.7 |
| BzAc, Acetophenone (AcPh), Adipic acid | (1/3)[3] | (2/5)[3] | 1.6 | 1.8 |
| BzAc, AcPh, Benzophenone | " | " | 1.2 | 1.3 |
| BzAc, AcPh, 2-Benzoyl benzoic acid | " | " | 1.7 | 1.7 |
| BzAc, AcPh, t-Butyl benzoic acid | " | " | 1.8 | 2.1 |
| BzAc, AcPh, Propiophenone | " | " | 1.6 | 1.7 |
| BzAc, AcPh, Salicylic acid | " | " | 1.5 | 1.7 |
| BzAc, AcPh, o-Toluic acid | " | " | 1.3 | 1.3 |
| BzAc, Benzonitrile, Cinnamic acid | " | " | 1.7 | 1.8 |
| BzAc, Butyl benzoate, Glutaric acid | " | " | 1.6 | 1.7 |
| BzAc, Isophorone, Salicylic | " | " | 1.7 | 1.9 |
| BzAc, Methyl benzoate, Butyl benzyl phthalate | " | " | 1.4 | 1.4 |
| BzAc, Methyl benzoate, Malic acid | " | " | 1.3 | 1.4 |
| BzAc, Methyl benzoate, o-Toluic acid | " | " | 1.5 | 1.6 |
| BzAc, Butyl benzyl phthalate, Salicylic acid | " | " | 1.8 | 2.1 |
| BzAc, Methyl salicylate (MeSal), Cinnamic acid | " | " | 1.4 | 1.5 |
| BzAc, MeSal, Glutaric acid | " | " | 1.5 | 1.5 |

TABLE 1-continued
Effective Extractive Distillation Agents

| Compounds | Ratios | | Relative Volatility | |
|---|---|---|---|---|
| BzAc, MeSal, Malic acid | " | " | 1.3 | 1.4 |
| BzAc, MeSal, Salicylic acid | " | " | 2.0 | 1.8 |
| BzAc, MeSal, Sebacic acid | " | " | 1.3 | 1.5 |
| Cinnamic acid (CnAc), Acetophenone (AcPh), Azelaic acid | " | " | 1.4 | 1.5 |
| CnAc, AcPh, Benzophenone | " | " | 1.6 | 2.3 |
| CnAc, AcPh, t-Butyl benzoic acid | " | " | 1.7 | 1.8 |
| CnAc, AcPh, Neopentanoic acid | " | " | 1.3 | 1.4 |
| CnAc, AcPh, Salicylic acid | " | " | 1.7 | 1.9 |
| CnAc, Methyl salicylate, 2-Benzoyl benzoic acid | " | " | 1.3 | 1.4 |
| CnAc, Methyl Salicylate Salicylic acid | " | " | 1.6 | 2.2 |
| CnAc, Benzophenone, 2,4-Pentanedione | " | " | 1.5 | 1.9 |
| CnAc, AcPh, Benzophenone, 2-Benzoyl benzoic acid, Acetophenone | (1/4)[4] (1/2)[2] | (1/3)[4] (3/5)[2] | 1.8 1.5 | 1.8 1.6 |
| 2-Benzoyl benzoic acid, Methyl salicylate | " | " | 1.5 | 1.4 |
| t-Butyl benzoic acid, Acetophenone | " | " | 1.7 | 1.6 |
| Glutaric acid (GlAc), Acetophenone | " | " | 1.7 | 1.9 |
| GlAc, Benzophenone | " | " | 1.4 | 1.8 |
| GlAc, Methyl salicylate | " | " | 1.4 | 1.5 |
| GlAc, Acetophenone, Benzophenone | (1/3)[3] | (2/5)[3] | 1.6 | 1.7 |
| GlAc, Acetophenone, p-tert. Butyl benzoic acid | " | " | 1.5 | 1.7 |
| Salicylic acid (salAc), Acetophenone | (1.2)[2] | (3/5)[2] | 1.6 | 1.8 |
| SalAc, Benzonitrile | " | " | 1.5 | 1.5 |
| SalAc, Isophorone | " | " | 1.4 | 1.6 |
| SalAc, Acetophenone, Butyl benzyl phthalate | (1/3)[3] | (2/5)[3] | 1.4 | 1.6 |
| SalAc, Benzonitrile, Glutaric acid | " | " | 1.5 | 1.4 |
| SalAc, Isophorone, Dipropylene glycol dibenzoate | " | " | 1.4 | 1.6 |
| SalAc, AcPh, Adipic acid, Propiophenone | (1/4)[4] | (1/3)[4] | 2.6 | 2.1 |
| Sebacic acid, Methyl salicylate | (1/2)[2] | (3/5)[2] | 1.5 | 1.5 |
| m-Toluic acid, Acetophenone | " | " | 1.5 | 1.8 |
| m-Toluic acid, Butyl benzoate | " | " | 1.5 | 1.8 |
| m-Toluic acid, Methyl benzoate | " | " | 1.4 | 1.4 |
| m-Toluic acid, Acetophenone, Neopentanoic acid | (1/3)[3] | (2/5)[3] | 1.5 | 1.8 |

TABLE 2
Data From Runs Made In Rectification Column

| Agent | Column | Time, hrs. | Weight % Water | Weight % Formic acid | Relative Volatility |
|---|---|---|---|---|---|
| 80% Heptanoic acid, 20% Azelaic acid | Overhead | 0.5 | 82.4 | 17.6 | |
| | Bottoms | | 64.1 | 35.9 | 1.24 |
| | Overhead | 1 | 98.1 | 1.9 | |
| | Bottoms | | 51.2 | 48.8 | 2.38 |
| | Overhead | 2 | 98.6 | 1.4 | |
| | Bottoms | | 53.3 | 46.7 | 2.50 |
| 67% Heptanoic acid, 16% Azelaic acid, 17% 2-Hydroxyacetophenone | Overhead | 0.5 | 64.1 | 35.9 | |
| | Bottoms | | 53.8 | 46.2 | 1.11 |
| | Overhead | 1 | 96.7 | 3.3 | |
| | Bottoms | | 49.3 | 50.7 | 2.15 |
| | Overhead | 2 | 97.9 | 2.1 | |
| | Bottoms | | 46.8 | 53.2 | 2.43 |

SUMMARY OF THE INVENTION

The objects of the invention are provided by a process for separating formic acid from water which entails the use of carboxylic acids admixed with certain high boiling organic compounds as the agents in extractive distillation.

DETAILED DESCRIPTION OF THE INVENTION

We have discovered that carboxylic acids admixed with other high boiling organic compounds, will effectively negate the formic acid-water maximum azeotrope and permit the separation of water from formic acid by rectification when employed as the agent in extractive distillation. Table 1 lists several carboxylic acids and their mixtures and the approximate proportions that I have found to be effective. The data in Table 1 was obtained in a vapor-liquid equilibrium still. In each case, the starting material was the formic acid-water azeotrope. The ratios are the parts by weight of extractive agent used per part of formic acid-water azeotrope. The relative volatilities are listed for each of the two ratios employed. The carboxylic acids which are effective when used in mixtures are hexanoic acid, heptanoic acid, octanoic acid, pelargonic acid, decanoic acid, neodecanoic acid, benzoic acid, cinnamic acid, 2-benzoyl benzoic acid, t-butyl benzoic acid, glutaric acid, salicylic acid, sebacic acid, neopentanoic acid, o-toluic acid, m-toluic acid and p-toluic acid.

The two relative volatilities shown in Table 1 correspond to the two different ratios investigated. For example, in Table 1, one half part of hexanoic acid mixed with one half part of acetophenone with one part of the formic acid-water azeotrope gives a relative volatility of 2.0, 3/5 parts of hexanoic acid plus 3/5 parts of acetophenone give 2.4. One third part of hexanoic acid plus ⅓ part of acetophenone plus ⅓ part of decanoic acid with one part of the formic acid-water azeotrope gives a relative volatility of 2.1, with 2/5 parts, these three give a relative volatility of 2.2. In every example in Table 1, the starting material is the formic acid-water azeotrope which possesses a relative volatility of 1.00.

One of the mixtures, heptanoic acid-azelaic acid, listed in Table 1 and whose relative volatility had been determined in the vapor-liquid equilibrium still, was then evaluated in a glass perforated plate rectification column possessing 4.5 theoretical plates and the results listed in Table 2. The data in Table 2 was obtained in the following manner. The charge was 85 wt.% formic acid and 15% water and after a half hour of operation in the 4.5 theoretical plate column to establish equilibrium, 80% heptanoic acid-20% azelaic acid at 95° C. and 20 ml/min. was pumped in. The rectification was continued with sampling of overhead and bottoms after ½ hour. The analysis is shown in Table 2 and was 82.4% water, 17.6% formic acid in the overhead and 64.1% water, 35.9% formic acid in the bottoms which gives a relative volatility of 1.24 of water to formic acid. After one hour of continuous operation, the overhead was 98.1% water, 1.9% formic acid, the bottoms was 51.2% water, 48.8% formic acid which is relative volatility of 2.38. After two hours of continuous operation, the overhead was 98.6% water, 1.4% formic acid, the bottoms was 53.3% water, 46.7% formic acid which is a relative volatility of 2.50. This indicates that the maximum azeotrope has been negated and separation accomplished. Without the extractive agent, the overhead would have approached the maximum azeotrope composition of 22.5% water. This proves that the extractive agent is negating the azeotrope and makes the rectification proceed as if the azeotrope no longer existed and brings the more volatile component, water, out as overhead. And this from formic acid which normally boils only 0.8° C. higher.

THE USEFULNESS OF THE INVENTION

The usefulness or utility of this invention can be demonstrated by referring to the data presented in Tables 1 and 2. All of the successful extractive distillation agents show that formic acid and water can be separated from their maximum azeotrope by means of distillation in a rectification column and that the ease of separation as measured by relative volatility is considerable. Without these extractive distillation agents, no improvements above the azeotrope composition will occur in the rectification column. The data also show that the most attractive agents will operate at a boilup rate low enough to make this a useful and efficient method of recovering high purity formic acid from any mixture with water including the maximum azeotrope. The stability of the compounds used and the boiling point difference is such that complete recovery and recycle is obtainable by a simple distillation and the amount required for make-up is small.

WORKING EXAMPLES

Example 1

Fifty grams of the formic acid-water azeotrope, 25 grams of hexanoic acid and 25 grams of acetopheone were charged to the vapor-liquid equilibrium still and refluxed for 16 hours. Analysis indicated a vapor composition of 71.6% water, 28.4% formic acid, a liquid composition of 56% water, 44% formic acid which is a relative volatility of 2.0. Five grams of hexanoic acid and five grams of acetophenone were added and refluxing continued for another twelve hours. Analysis indicated a vapor composition of 72.7% water, 27.3% formic acid, a liquid composition of 53.1% water, 46.9% formic acid which is a relative volatility of 2.4.

Example 2

Fifty grams of the formic acid-water azeotrope, 17 grams of hexanoic acid, 17 grams of acetophenone and 17 grams of decanoic acid were charged to the vapor-liquid equilibrium still and refluxed for 16 hours. Analysis indicated a vapor composition of 59.7% water, 40.3% formic acid, a liquid composition of 41.5% water, 58.5% formic acid which is a relative volatility of 2.1. Three grams each of hexanoic acid, acetophenone and decanoic acid were added and refluxing continued for another eleven hours. Analysis indicated a vapor composition of 60.5% water, 39.5% formic acid, a liquid composition of 41% water, 59% formic acid which is a relative volatility of 2.2.

Example 3

A glass perforated plate rectification column was calibrated with ethylbenzene and p-xylene which possesses a relative volatility of 1.06 and found to have 4.5 theoretical plates. A solution comprising 340 grams of formic acid and 60 grams of water was placed in the stillpot and heated. When refluxing began, an extractive agent comprising 80% heptanoic acid and 20% azelaic acid was pumped into the column at a rate of 20 ml/min. The temperature of the extractive agent as it entered the column was 95° C. After establishing the feed rate of the extractive agent, the heat input to the formic acid and water in the stillpot was adjusted to give a total reflux rate of 10–20 ml/min. After one hour of operation, the overhead and bottoms samples of approximately two ml. were collected and analysed by gas chromatography. The overhead analysis was 98.1% water. 1.9% formic acid. The bottoms analysis was 51.2% water, 48.8% formic acid. Using these compositions in the Fenske equation, with the number of theoretical plates in the column being 4.5, gave an average relative volatility of 2.38 for each theoretical plate. After two hours of total operating time, the overhead and bottoms samples were again taken and analysed. The overhead composition was 98.6% water, 1.4% formic acid and the bottoms composition was 53.3% water, 46.7% formic acid. This gave an average relative volatility of 2.50 for each theoretical plate.

Example 4

Using the same column as in Example 3, an extractive agent consisting of 67% heptanoic acid, 16% azelaic acid and 17% 2-hydroxyacetophenone was pumped into the column at a rate of 20 ml/min. After one hour of operation, the overhead analysis was 96.7% water, 3.3% formic acid, the bottoms composition was 49.3% water, 50.7% formic acid which is an average relative volatility of 2.15. After two hours of total operating time, the overhead composition was 97.9% water, 2.1% formic acid, the bottoms composition was 46.8% water, 53.2% formic acid which is an average relative volatility of 2.43 for each theoretical plate.

The data for Examples 3 and 4 is shown in Table 2.

We claim:

1. A method for recovering formic acid from mixtures of formic acid and water which comprises distilling a mixture of formic acid and water in a rectification column in the presence of about one part of an extractive agent per part of formic acid-water mixture, recovering water as overhead product and obtaining the formic acid and the extractive agent from the stillpot, wherein said extractive agent comprises a mixture of 2-benzoylbenzoic acid and methyl salicylate.

* * * * *